(12) United States Patent
Aslund et al.

(10) Patent No.: US 9,149,539 B1
(45) Date of Patent: Oct. 6, 2015

(54) CRYSTALLINE NALOXOL-PEG CONJUGATE

(71) Applicants: AstraZeneca AB, Macclesfield, Chesire (GB); Nektar Therapeutics, San Francisco, CA (US)

(72) Inventors: Bengt Aslund, Sodertalje (SE); Carl-Johan Aurell, Sodertalje (SE); Martin Hans Bohlin, Sodertalje (SE); Tesfai Sebhatu, Sodertalje (SE); Bo Ingvar Ymen, Sodertalje (SE); Eric Thomas Healy, Madison, AL (US); David Richard Jensen, Harvest, AL (US); David Thomas Jonaitis, Brookston, IN (US); Stephan Parent, West Lafayette, IN (US)

(73) Assignees: ASTRAZENECA AB, Sodertalje (SE); NEKTAR THERAPEUTICS, San Francisco, CA (US)

( * ) Notice: Subject to any disclaimer, the term of this patent is extended or adjusted under 35 U.S.C. 154(b) by 0 days.

(21) Appl. No.: 14/645,347

(22) Filed: Mar. 11, 2015

Related U.S. Application Data

(63) Continuation of application No. 13/823,953, filed as application No. PCT/SE2011/051161 on Sep. 29, 2011, now Pat. No. 9,012,469.

(60) Provisional application No. 61/388,501, filed on Sep. 30, 2010.

(51) Int. Cl.
C07D 489/04 (2006.01)
A61K 47/48 (2006.01)
C07C 55/07 (2006.01)

(52) U.S. Cl.
CPC ........... A61K 47/48215 (2013.01); C07C 55/07 (2013.01); C07D 489/04 (2013.01)

(58) Field of Classification Search
USPC .......................................................... 546/44
See application file for complete search history.

(56) References Cited

U.S. PATENT DOCUMENTS

| | | |
|---|---|---|
| 7,056,500 B2 | 6/2006 | Bentley et al. |
| 7,662,365 B2 | 2/2010 | Bentley et al. |
| 7,786,133 B2 | 8/2010 | Bentley et al. |
| 8,034,825 B2 | 10/2011 | Bentley et al. |
| 8,067,431 B2 | 11/2011 | Fishburn et al. |
| 8,183,376 B2 | 5/2012 | Cheng et al. |
| 8,349,307 B2 | 1/2013 | Bentley et al. |
| 8,440,687 B2 | 5/2013 | Riggs-Sauthier et al. |
| 8,563,726 B2 | 10/2013 | Cheng et al. |
| 8,617,530 B2 | 12/2013 | Roberts et al. |
| 2002/0182172 A1 | 12/2002 | Bentley et al. |
| 2003/0044402 A1 | 3/2003 | Nelson |
| 2003/0105275 A1 | 6/2003 | Bentley et al. |
| 2004/0023852 A1 | 2/2004 | Roberts et al. |
| 2004/0082620 A1 | 4/2004 | Craig et al. |
| 2005/0136031 A1 | 6/2005 | Bentley et al. |
| 2006/0182692 A1 | 8/2006 | Fishburn et al. |
| 2010/0210676 A1 | 8/2010 | Fishburn et al. |
| 2012/0264775 A1 | 10/2012 | Riggs-Sauthier et al. |
| 2014/0303403 A1 | 10/2014 | Bentley et al. |
| 2015/0038524 A1 | 2/2015 | Aslund et al. |

FOREIGN PATENT DOCUMENTS

| | | |
|---|---|---|
| EP | 0995757 A2 | 4/2000 |
| WO | 99/30727 A1 | 6/1999 |
| WO | 01/19407 A2 | 3/2001 |
| WO | 01/47562 A2 | 7/2001 |
| WO | 01/62299 A2 | 8/2001 |
| WO | 02/065988 A2 | 8/2002 |
| WO | 02/089789 A2 | 11/2002 |
| WO | 02/098451 A1 | 12/2002 |
| WO | 02/098452 A1 | 12/2002 |
| WO | 03/032990 A2 | 4/2003 |
| WO | 03/037384 A2 | 5/2003 |
| WO | 03/037385 A1 | 5/2003 |
| WO | 03/084504 A1 | 10/2003 |
| WO | 2005/012335 A1 | 2/2005 |
| WO | 2005/058367 A2 | 6/2005 |

(Continued)

OTHER PUBLICATIONS

Berge et al., "Pharmaceutical Salts," J. Pharm. Sci. (Jan. 1977), pp. 132-150, vol. 66, No. 1.
Brittain et al., "Polymorphism in Pharmaceutical Solids", Second Ed., (2009), pp. 334-335, Informa Healthcare, New York.
Eldon et al., "NKTR-118 (Oral PEG-Naloxol), a PEGylated Derivative of Naloxone: Demonstrations of Selective Peripheral Opioid Antagonism After Oral Administration in Preclinical Models," Poster 28 presented at the American Academy of Pain Management 18th Annual Clinical Meeting, (Sep. 27-30, 2007), Las Vegas, NV.
Erez et al., "Narcotic Antagonistic Potency of Bivalent Ligands Which Contain B-Naltrexarnine. Evidence for Bridging between Proximal Recognition Sites", J. Medicinal Chemistry, (1982), pp. 847-849, vol. 25, No. 7.
European Searching Authority, "Supplementary Search Report for International Application No. EP 11829686," (Aug. 18, 2014), 10 pages.

(Continued)

Primary Examiner — Charanjit Aulakh
(74) Attorney, Agent, or Firm — Jones Day

(57) ABSTRACT

Naloxol-polyethylene glycol conjugates of the formula:

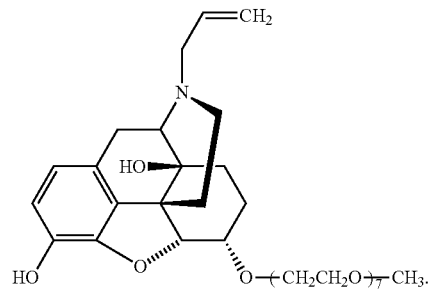

Figure 1:
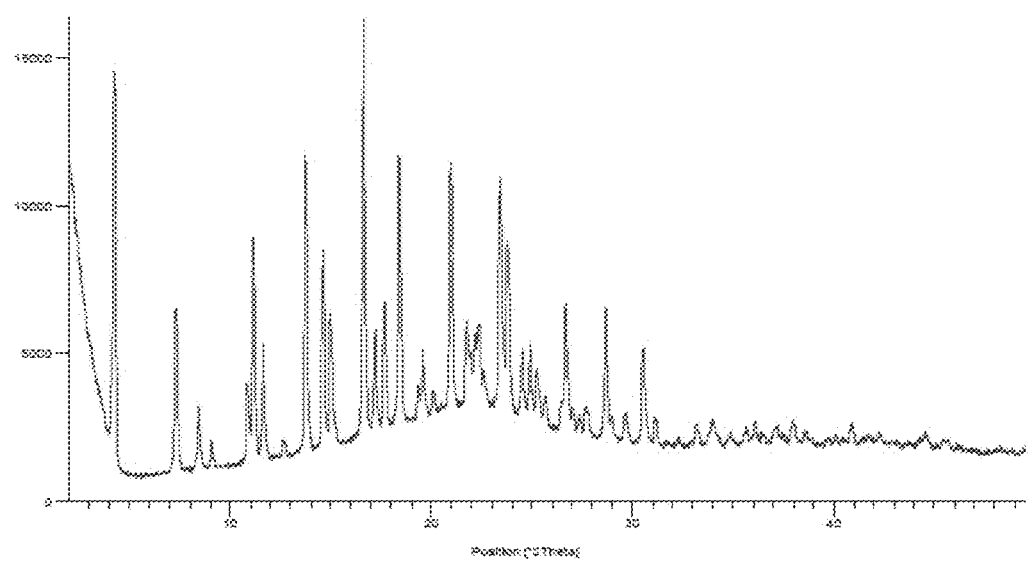

are provided in oxalate or phosphate salt forms including crystalline forms. Methods of preparing the salt forms and pharmaceutical compositions comprising the salt forms are also provided.

1 Claim, 3 Drawing Sheets

(56) References Cited

FOREIGN PATENT DOCUMENTS

| WO | 2005/051327 A1 | 9/2005 |
|---|---|---|
| WO | 2008/057579 A2 | 5/2008 |
| WO | 2009/137086 A1 | 11/2009 |

OTHER PUBLICATIONS

Feinberg et al., "The Opiate Receptor: A Model Explaining Structure-Activity Relationships of Opiate Agonists and Antagonists," Proc Natl Acad Sci, USA, (1976), pp. 4215-4219, vol. 73, No. 11.

Ganong, "Review of Medical Physiology," (1991), 15th Edition, pp. 566-567.

International Centre for Trade and Sustainable Development (ICTSD) et al., Guidelines for the examination of pharmaceutical patents: developing a public health perspective—A Working Paper, by C. Correa, (Jan. 2007), 56 pages, available at http://ictsd.org/i/publications/11393/?view=document.

International Searching Authority, "International Search Report for International Application No. PCT/SE2011/051161," (Mailed Jan. 1, 2012), 4 pages.

Interntaional Searching Authority, "Written Opinion for International Application No. PCT/SE2011/051161," (Mailed Dec. 19, 2011), 5 pages.

Jiang et al., "Stereochemical Studies on Medicinal Agents, 23.1 Synthesis and Biological Evaluation of 6-Amino Derivatives of Naloxone and Naltrexone," J. Medicinal Chemistry, (1977), pp. 1100-1103, vol. 20, No. 8.

Lahiani-Skiba et al., "Solubility and dissolution rate of progesterone-cyclodextrin-polymer systems," Drug Dev. Ind. Pharm., (2006), pp. 1043-4058, vol. 32, No. 9.

Neumann et al., "Clinical Investigation of NKTR-118 as a Selective Oral Peripheral Opioid Antagonist," Poster 27 Presented at the American Academy of Pain Management 18th Annual Clinical Meeting, (Sep. 27-30, 2007), Las Vegas, NV.

Liu, R., "Water-Insoluble Drug Formulation," 2nd Edition (2008), pp. 166-168, CRC Press/Taylor & Francis Group, Boca Raton, Florida USA.

Odinees et al., "NKTR-118, An Oral 15 Peripheral Opioid antagonist, Has Low Potential for Drug-Drug Interactions," Journal of Clinical Phamacology, (Sep. 13-15, 2009), p. 1123, vol. 49, No. 9, Post 28, 38th Annual Meeting of the American-College-of-Clinical-Pharmacology, San Antonio, TX.

Odinees, A., et al., "Comparative 15 Bioavailability of NKTR-118 Tables and Solution: A Case of Bioequivalence Between Dosage Froms from a Rapidly Absorbed Drug," Journal of Clinical Pharmacology, (Sep. 13-15, 2009), p. 1123, vol. 49, No. 9, Post 27, 38th Annual Meeting of the American-College-of-Clinical-Pharmacology, San Antonio, TX.

Olde et al., "Affinity Partitioning and Centrifugal Counter-Current Distribution of Membrane-Bound Opiate Receptors Using Naloxone-Poly(Ethylene Glycol)", Neuroscience, (1985), pp. 1247-1253, vol. 15, No. 4.

Wang et al., "Inverse Agonists and Neutral Antagonists at . . . ," Journal of Neurochemistry, (2001), pp. 1590-1600, vol. 77, No. 6.

Webster et al., "NKTR-118 Significantly Reverses Opioid-Induced Constipation," Poster 39, 20th AAPM Annual Clinical Meeting, (Oct. 10, 2009), Phoenix, AZ, 1 page.

Yamashita et al., "Micelle Monomer Control over the Membrane-Disrupting Properties of an Amphiphilic Antibiotic", J. Am. Chem. Soc., (1995), pp. 6249-6253, vol. 117, No. 23.

CRYSTALLINE NALOXOL-PEG CONJUGATE

1. RELATED APPLICATION

This application is a continuation of U.S. patent application Ser. No. 13/823,953, filed Sep. 4, 2013, which is a 371 of International Patent Application No. PCT/SE2011/051161, filed Sep. 29, 2011, which claims the benefit of priority to U.S. Provisional Application No. 61/388,501, filed Sep. 30, 2010, which are hereby incorporated by reference in their entireties into this application.

2. TECHNICAL FIELD

Naloxol-polyethylene glycol conjugates are provided herein in solid phosphate and oxalate salt forms. Methods of preparing the salt forms, and pharmaceutical compositions comprising the salt forms are also provided herein.

3. BACKGROUND

Effective pain management therapy often calls for an opioid analgesic. In addition to the desired analgesic effect, however, certain undesirable side effects, such as bowel dysfunction, nausea, constipation, among others, can accompany the use of an opioid analgesic. Such side effects may be due to opioid receptors being present outside of the central nervous system, principally in the gastrointestinal tract. Clinical and preclinical studies support the use of $mPEG_7$-O-naloxol, a conjugate of the opioid antagonist naloxol and polyethylene glycol, to counteract undesirable side effects associated with use of opioid analgesics. When administered orally to a patient $mPEG_7$-O-naloxol largely does not cross the blood brain barrier into the central nervous system, and has minimal impact on opioid-induced analgesia. See, e.g., WO 2005/058367; WO 2008/057579; Webster et al., "NKTR-118 Significantly Reverses Opioid-Induced Constipation," Poster 39, 20th AAPM Annual Clinical Meeting (Phoenix, Ariz.), Oct. 10, 2009.

To move a drug candidate such as $mPEG_7$-O-naloxol to a viable pharmaceutical product, it is important to understand whether the drug candidate has polymorphic forms, as well as the relative stability and interconversions of these forms under conditions likely to be encountered upon large-scale production, transportation, storage and pre-usage preparation. Solid forms of a drug substance are often desired for their convenience in formulating a drug product. No solid form of $mPEG_7$-O-naloxol drug substance has been made available to date, which is currently manufactured and isolated as an oil in a free base form. Exactly how to accomplish this is often not obvious. For example the number of pharmaceutical products that are oxalate salts is limited. The free base form of $mPEG_7$-O-naloxol has not been observed to form a crystalline phase even when cooled to $-60°$ C. and has been observed to exist as a glass with a transition temperature of approximately $-45°$ C. Furthermore, $mPEG_7$-O-naloxol in its free base form can undergo oxidative degradation upon exposure to air. Care can be taken in handling the free base, for example, storing it under inert gas, to avoid its degradation. However, a solid form of $mPEG_7$-O-naloxol, preferably one that is stable when kept exposed to air, is desired.

SUMMARY OF THE INVENTION

In one aspect, provided herein are solid salt forms of $mPEG_7$-O-naloxol.

In another aspect, provided herein are methods of producing a naloxol-polyethylene glycol conjugate oxalate salt, the salt comprising ionic species of $mPEG_7$-O-naloxol and oxalic acid. The formulas of $mPEG_7$-O-naloxol and oxalic acid are as follows:

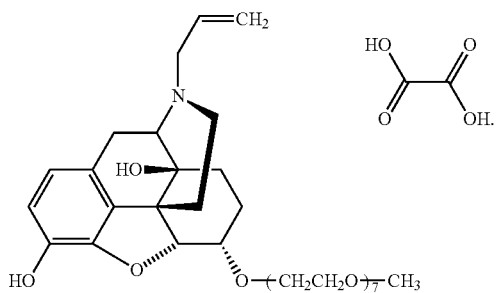

In certain embodiments, the methods provided comprise dissolving $mPEG_7$-O-naloxol free base in ethanol; adding methyl t-butyl ether to the dissolved $mPEG_7$-O-naloxol solution; adding oxalic acid in methyl t-butyl ether to the dissolved $mPEG_7$-O-naloxol over a period of at least 2 hours to produce a slurry; and filtering the slurry to yield the naloxol-polyethylene glycol conjugate oxalate salt in solid form.

In certain embodiments, the methods provided comprise dissolving $mPEG_7$-O-naloxol free base in acetonitrile; adding water to the dissolved $mPEG_7$-O-naloxol solution; adding oxalic acid in ethyl acetate to the dissolved $mPEG_7$-O-naloxol over a period of at least 2 hours to produce a slurry; and filtering the slurry to yield the naloxol-polyethylene glycol conjugate oxalate salt in solid form.

In some embodiments, the solid salt form of $mPEG_7$-O-naloxol is a crystalline form.

In certain embodiments a solid crystalline salt provided herein is substantially pure, having a purity of at least about 80%, at least about 85%, at least about 90%, at least about 92%, at least about 95%, at least about 96%, at least about 97%, at least about 98%, or at least about 99%.

In certain embodiments, the solid salt form of $mPEG_7$-O-naloxol is a phosphate salt.

In other embodiments, the solid $mPEG_7$-O-naloxol salt form is an oxalate salt. For instance, in some embodiments of solid oxalate salt forms provided herein, the solid $mPEG_7$-O-naloxol oxalate salt form is in Form A, as described herein. As another example, in some embodiments of solid oxalate salt forms provided herein, the solid $mPEG_7$-O-naloxol oxalate salt form is in Form B, as described herein.

In yet other embodiments, an oxalate salt of $mPEG_7$-O-naloxol in solid form prepared according to the methods described herein is provided.

In yet other embodiments, an dihydrogenphosphate salt of $mPEG_7$-O-naloxol in solid form prepared according to the methods described herein is provided.

In certain embodiments of a solid $mPEG_7$-O-naloxol oxalate salt Form B provided herein, the salt form exhibits a single endothermic peak on differential scanning calorimetry between room temperature and about $150°$ C. The single endothermic peak can occur, for instance, between about $91°$ C. to about $94°$ C. For example, in some embodiments the endothermic peak is at about $92°$ C., about $92.5°$ C., or about $93°$ C.

Figure 2:
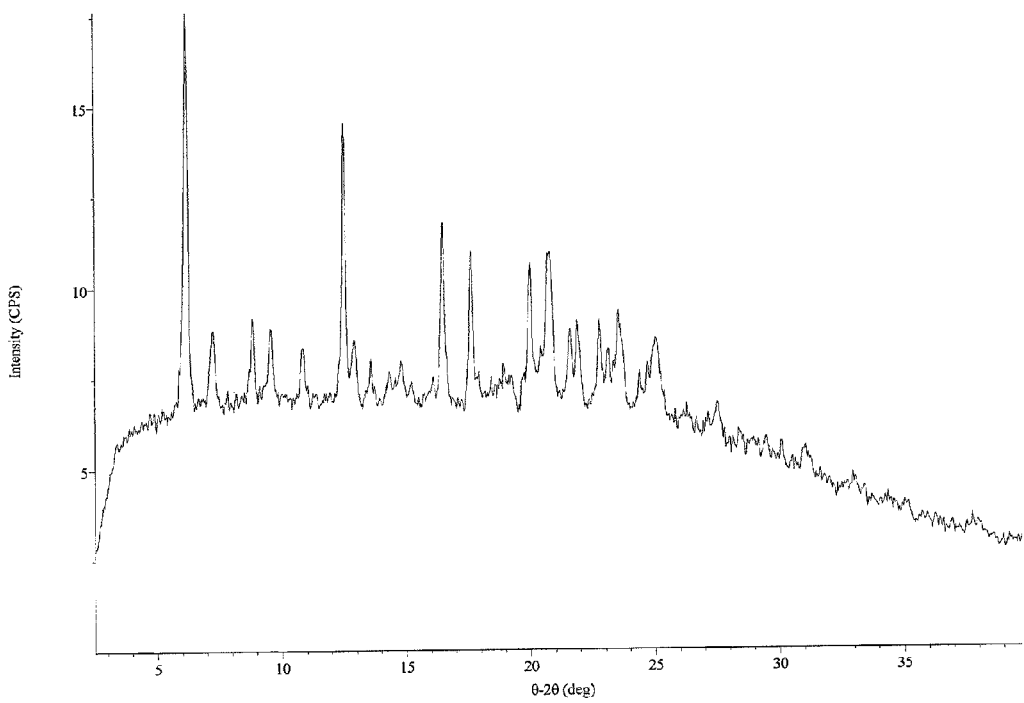

In yet other embodiments of a solid $mPEG_7$-O-naloxol oxalate salt Form A has an XRPD pattern as that in FIG. 2.

Figure 3:
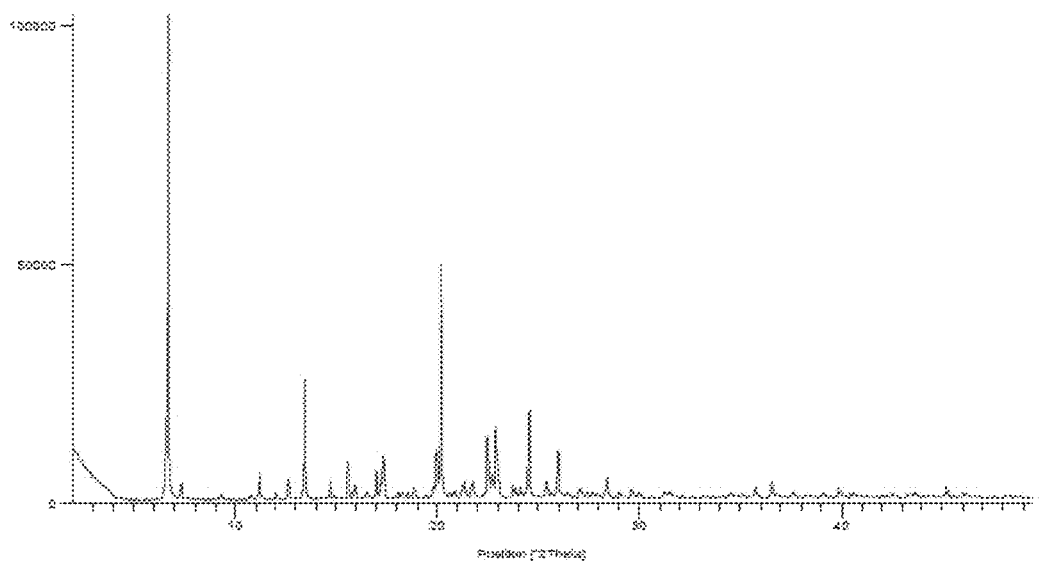

In yet other embodiments of a solid mPEG$_7$-O-naloxol oxalate salt Form B has an XRPD pattern as that in FIG. 3.

In yet other embodiments of a solid mPEG$_7$-O-naloxol dihydrogenphosphate salt it has an XRPD pattern as that in FIG. 1.

In another aspect, provided herein are pharmaceutical compositions comprising a solid mPEG$_7$-O-naloxol salt form and a pharmaceutically acceptable excipient. In some embodiments, pharmaceutical compositions provided herein are formulated for oral administration to a subject in a solid form.

4. DESCRIPTION OF THE DRAWINGS

FIG. 1 provides an X-ray powder diffraction (XRPD) diffractogram of crystalline mPEG$_7$-O-naloxol dihydrogenphosphate salt.

FIG. 2 provides an XRPD diffractogram of crystalline mPEG$_7$-O-naloxol oxalate salt form A.

FIG. 3 provides an XRPD diffractogram of crystalline mPEG$_7$-O-naloxol oxalate salt form B.

5. DETAILED DESCRIPTION

Provided herein are solid forms of an mPEG$_7$-O-naloxol salt, including, for example, phosphate salt and oxalate salt forms. There are a limited number of oxalate salts as pharmaceutical products. Methods of preparing solid salt forms of mPEG$_7$-O-naloxol are also provided. The solid salt forms include, for instance, substantially pure crystalline forms. Certain methods of preparing mPEG$_7$-O-naloxol provided herein can be adapted to manufacturing scale production of mPEG$_7$-O-naloxol oxalate salt in crystalline form. As demonstrated in the following examples, for instance with a solid oxalate salt form, solid mPEG$_7$-O-naloxol salt forms can be stable and can produce little or no oxidative degradation product under conditions that produce oxidative degradation product in mPEG$_7$-O-naloxol free base. The salt formation produces a purer product, which is substantially free from other chemical compounds. Initial crystallization efforts did not yield a pure product and numerous methods were attempted before a successful result was achieved. In addition various acids were attempted before success was achieved with oxalic and phosphoric acids to produce the corresponding salts. Furthermore, it is believed that an oxalate salt will increase the likelihood of success for manufacturing purposes. Pharmaceutical compositions comprising the mPEG$_7$-O-naloxol solid salt forms are also provided herein.

5.1 Terminology

Abbreviations used herein include the following: DCM, dichloromethane; DMF, dimethylformamide; DSC, differential scanning calorimetry; DVS, dynamic vapor sorption; EtOAc, ethyl acetate; IPA, 2-propanol; IPE, diisopropyl ether; MEK, methyl ethyl ketone; MeOH, methanol; MeTHF, 2-methyltetrahydrofuran; MIBK, methyl isobutyl ketone; MTBE, methyl t-butyl ether; mPEG, methyl-capped polyethylene glycol; PEG, polyethylene glycol; PrCN, n-propyl cyanide; RH, relative humidity; THF, tetrahydrofuran; and XRPD, X-ray powder diffraction.

To facilitate understanding of the disclosure set forth herein, a number of terms are defined below. Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

As used herein, the terms "mPEG$_7$-O-naloxol" "α-6-mPEG$_7$-O-naloxol" and "α-6-CH$_3$—(OCH$_2$CH$_2$)$_7$—O-naloxol" are used synonymously to refer to a compound having the formula:

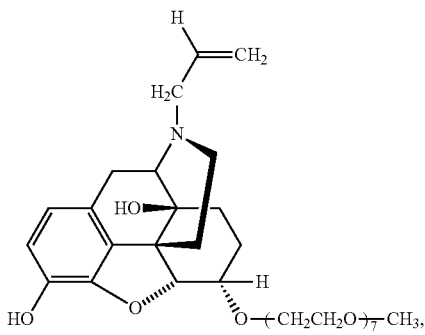

which, unless otherwise stated or apparent from the context in which it is used, means in its free base form. A salt of mPEG$_7$-O-naloxol, is an ionic form of mPEG$_7$-O-naloxol that exists with a counterion produced from, in this case, an acid. The counterion produced from the acid is variously referred to herein as an "acid counterion" or just "counterion." When, for example, the acid counterion is that of oxalic acid, the mPEG$_7$-O-naloxol salt is an oxalate salt. Oxalic acid has the formula:

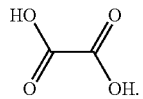

When, for example, the acid counterion is that of phosphoric acid, the mPEG$_7$-O-naloxol salt is a phosphate salt. There can be three types of phosphate salts; dihydrogenphosphate; hydrogenphosphate and phosphate. Accordingly, one, two or three hydrogens have been removed.

Without intending to be limited by any theory or mechanism, it is believed that an ionic species of mPEG$_7$-O-naloxol may include species where the nitrogen accepts a proton, having the formula:

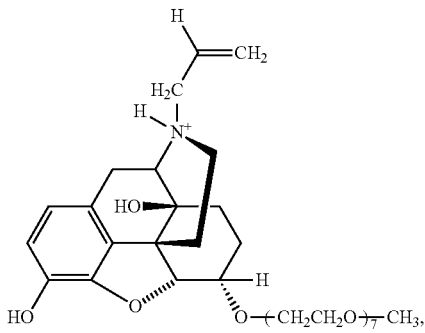

Without intending to be limited by any theory or mechanism, it is believed that an ionic species of oxalic acid may include those where one or more hydrogens are removed, for instance:

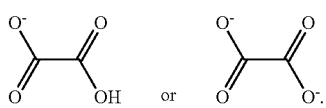

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, within 10%, within 5%, within 4%, within 3%, within 2%, within 1%, or within 0.5% of the specified dose, amount, or weight percent.

As used herein, and unless otherwise specified, the terms "about" and "approximately," when used in connection with a numeric value or range of values which is provided to describe a particular solid form, e.g., a specific temperature or temperature range, such as, for example, that describing a melting, dehydration, desolvation or glass transition; a mass change, such as, for example, a mass change as a function of temperature (TGA) or humidity (DVS); a solvent or water content, in terms of, for example, mass or a percentage; or a peak position, such as, for example, in analysis by, for example, differential scanning calorimetry (DSC), thermogravimetric analysis or powder X-ray powder diffraction (XRPD); indicate that the value or range of values may deviate to an extent deemed reasonable to one of ordinary skill in the art while still describing the particular solid form. Specifically, the terms "about" and "approximately," when used in this context, indicate that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form.

The term "amorphous" or "amorphous form" is intended to mean that the substance, component, or product in question is not substantially crystalline as determined, for instance, by XRPD or where the substance, component, or product in question, for example is not birefringent or cubic when viewed using a polarized light microscope. In certain embodiments, a sample comprising an amorphous form of a substance may be substantially free of other amorphous forms and/or crystalline forms.

The term "crystalline form" refers to a crystalline solid of a chemical compound, including, but not limited to, a single-component or multiple-component crystal, and/or a polymorph, a solvate, a hydrate, a clathrate, a co-crystal, a salt of a compound, solvates of salts, hydrates of salts. Crystalline forms of a substance can be obtained by a number of methods, as known in the art. Such methods include, but are not limited to, melt crystallization, melt cooling, solvent crystallization, crystallization in confined spaces such as, e.g., in nanopores or capillaries, crystallization on surfaces or templates such as, e.g., on polymers, crystallization in the presence of additives, such as, e.g., co-crystal counter-molecules, desolvation, dehydration, rapid evaporation, rapid cooling, slow cooling, vapor diffusion, sublimation, reaction crystallization, antisolvent addition, grinding and solvent-drop grinding.

Techniques for characterizing crystal forms and amorphous forms include, but are not limited to, thermal gravimetric analysis (TGA), differential scanning calorimetry (DSC), X-ray powder diffractometry (XRPD), single crystal X-ray diffractometry, vibrational spectroscopy, e.g., infrared (IR) and Raman spectroscopy, solid-state NMR, optical microscopy, hot stage optical microscopy, scanning electron microscopy (SEM), electron crystallography and quantitative analysis, particle size analysis (PSA), surface area analysis, solubility studies and dissolution studies.

As used herein and unless otherwise indicated, the term "hydrate" means a compound or salt thereof, further including a stoichiometric or non-stoichiometric amount of water bound by non-covalent intermolecular forces. As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate, and the like).

The term "pharmaceutically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

The term "polymorph" or "polymorphic form" refers to one of two or more crystal forms that comprise the same molecule, molecules or ions. Different polymorphs may have different physical properties such as, for example, melting temperatures, heats of fusion, solubilities, dissolution rates, and/or vibrational spectra as a result of the arrangement or conformation of the molecules or ions in the crystal lattice. The differences in physical properties exhibited by polymorphs may affect pharmaceutical parameters, such as storage stability, compressibility, density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph), mechanical changes (e.g., tablets crumble on storage as a kinetically favored polymorph converts to thermodynamically more stable polymorph), or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of a crystalline form may be important in processing; for example, one polymorph might be more likely to form solvates or might be difficult to filter and wash free of impurities (e.g., particle shape and size distribution might be different between polymorphs). As used herein and unless otherwise indicated, the term "stereomerically pure" means a composition that comprises one stereoisomer of a compound and is substantially free of other stereoisomers of that compound. In certain embodiments stereomerically pure α-6-mPEG$_7$-O-naloxol or salt thereof is provided herein that is substantially free of other stereoisomers including, for example, β-6-mPEG$_7$-O-naloxol or salt thereof. In certain embodiments, a stereomerically pure compound or salt thereof comprises greater than about 80 percent by weight of one stereoisomer of the compound and less than about 20 percent by weight of other stereoisomers of the compound, greater than about 90 percent by weight of one stereoisomer of the compound and less than about 10 percent by weight of the other stereoisomers of the compound, greater than about 95 percent by weight of one stereoisomer of the compound and less than about 5 percent by weight of the other stereoisomers of the compound, greater than about 97 percent by weight of one stereoisomer of the compound and less than about 3 percent by weight of the other stereoisomers or greater than about 99 percent by weight of one stereoisomer of the compound and less than about 1 percent by weight of the other stereoisomers of the compound. In certain embodiments, the term "stereomerically pure" mPEG$_7$-O-naloxol means that the compound is made up of approximately 100% by weight of α-6-mPEG$_7$-O-naloxol. The above percentages are based on the total amount of combined stereoisomers of the compound.

As used herein, a crystalline or amorphous form that is "pure," i.e., substantially free of other crystalline or amorphous forms, contains less than about 15 percent by weight of one or more other crystalline or amorphous forms, less than about 10 percent by weight of one or more other crystalline or amorphous forms, less than about 5 percent by weight of one or more other crystalline or amorphous forms, less than about 3 percent by weight of one or more other crystalline or amorphous forms, less than about 1 percent by weight of one or more other crystalline or amorphous forms, or less than about 0.5 percent by weight of one or more other crystalline or amorphous forms. In certain contexts, as used herein, "substantially pure" mPEG$_7$-O-naloxol salt can mean free of organic impurities, for example, unreacted precursors and side products or oxidative degradation products that might be present in the process for preparing mPEG$_7$-O-naloxol free base, or formed during storage of mPEG$_7$-O-naloxol free base. Organic impurities can include, for example, α-6-naloxol, naloxol conjugated to 4, 5, 6 or 8 polyethylene glycol subunits (i.e., ethylene oxide monomers), and so forth. An oxidative degradation product of mPEG$_7$-O-naloxol free base can, for instance, be glycidaldehyde. In certain embodiments, "substantially pure" means less than 100 ppm, less than 50 ppm, less than 25 ppm, 5 ppm, less than about 2 ppm or less then about 1 ppm of glycidaldehyde. As such, "substantially pure" mPEG$_7$-O-naloxol salt may comprise, in certain embodiments, less than about 10%, 5%, 3%, 2%, 1%, 0.75%, 0.5%, 0.25%, or 0.1% by weight of one or more other crystal forms and amorphous forms of the compound and/or other chemical compounds. In certain embodiments, a solid form that is substantially pure is substantially free of one or more other particular crystal forms, amorphous forms, and/or other chemical compounds.

The terms "subject," "patient" and "individual" as used herein are interchangeable and refer to a living organism suffering from or prone to a condition that can be prevented or treated by administration of a peripherally acting opioid antagonist, and includes both humans and animals. Such a condition can include, for example, an opioid-induced effect, e.g., bowel dysfunction, nausea, pruritis, or constipation. The terms "treat," "treating," and "treatment," as used herein with reference to mPEG$_7$-O-naloxol, are meant to include alleviating or abrogating one or more opioid-induced effects, e.g., bowel dysfunction, nausea, pruritis, or constipation, in a subject taking one or more opioid analgesics, where the subject taking the one or more opioid analgesics experiences, or continues to experience, opioid-induced analgesia.

The terms "prevent," "preventing," and "prevention," as used herein with reference to mPEG$_7$-O-naloxol, are meant to include decreasing a likelihood of occurrence, or of decreasing the severity, of one or more opioid-induced effects, e.g., bowel dysfunction, nausea, pruritis, or constipation, in a subject taking one or more opioid analgesics, where the subject taking the one or more analgesics experiences, or continues to experience, opioid-induced analgesia.

The term "therapeutically effective amount" is meant to include the amount of mPEG$_7$-O-naloxol salt that, when administered to a subject, is sufficient to prevent development of, or alleviate to some extent, one or more opioid-induced effects, e.g., bowel dysfunction, nausea, pruritis, or constipation, in the subject when administered one or more opioid analgesics, where the individual taking the one or more analgesics experiences, or continues to experience, opioid-induced analgesia. As used herein, it will be understood that reference to a central analgesic effect means the central analgesic effect associated within an opioid-treated subject (i.e., a subject receiving opioid-based analgesia via administration of one or more opioid analgesics). To achieve a central analgesic effect, the subject will typically be administered an opioid agonist. The opioid agonist can be administered to the subject by any suitable means, including, for example, by injection (e.g., intravenously, intraarterially, subdermally, intraperitoneally, intramuscularly or subcutaneously), orally, buccally, nasally, transmucosally, topically, via an ophthalmic preparation, or by inhalation. Administration of the opioid agonist can be achieved via self administration by the subject as well as by another person. The therapeutically effective dose (including frequency of dosing) of the opioid agonist will typically be in accordance with conventional administration schemes associated with the specific opioid and available, for example, in *Drug Facts and Comparisons 2010* (Wolters Kluwer Health/Facts & Comparisons®, St. Louis, Mo., USA).

As used herein, an "opioid agonist" is any natural or synthetic alkaloid or structural derivative of opium that activates one or more opioid receptor types. In some embodiments, an opioid agonist is also an "opioid analgesic," which, as used herein, means an opioid agonist that, when administered to a subject, produces some level of analgesia or relief of pain however short or long lasting for the subject. The opioid agonist can be a natural alkaloid such as penanthrene (e.g., morphine), or benzylisoquinoline (e.g., papaverine), a semi-synthetic derivative (e.g., hydromorphone), or any of various classes of synthetic derivatives (e.g., phenylpiperidines, benzmorphans, priopionanilides, and morphinans). Exemplary opioid agonists include alfentanil, bremazocine, buprenorphine, butorphanol, codeine, cyclazocine, dezocine, diacetylmorphine (i.e., heroin), dihydrocodeine, fentanyl, hydrocodone, hydromorphone, levorphanol, meperidine (pethidine), methadone, morphine, nalbuphine, noscapine, oxycodone, oxymorphone, papaverine, pentazocine, pethidine, phenazocine, propiram, propoxyphene, sufentanil, thebaine and tramadol. Preferably, the opioid agonist is selected from the group consisting of morphine, codeine, oxycodone, hydrocodone, dihydrocodeine, propoxyphene, fentanyl, and tramadol.

5.2 Embodiments

In one aspect, a solid salt form of mPEG$_7$-O-naloxol is provided. In certain embodiments, the solid salt form of mPEG$_7$-O-naloxol is crystalline. In some embodiments, the solid salt form is an mPEG$_7$-O-naloxol phosphate salt. In other embodiments, the solid salt form is a mPEG$_7$-O-naloxol oxalate salt.

In another aspect, provided herein are methods of producing a naloxol-polyethylene glycol conjugate oxalate salt, wherein the salt comprises ionic species of mPEG$_7$-O-naloxol and oxalic acid, which have the formula:

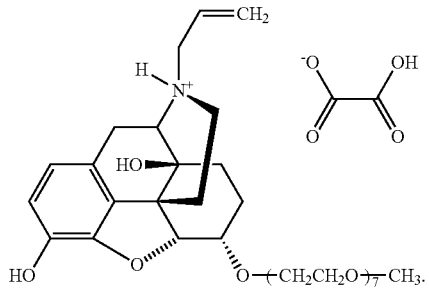

In other embodiments, an mPEG$_7$-O-naloxol oxalate salt is provided. In some embodiments, the mPEG$_7$-O-naloxol oxalate salt is in a solid form, which can, for example, be in an amorphous form, single crystalline form, multi-cyrstalline form, or mixed amorphous and crystalline form. Preferably, the mPEG$_7$-O-naloxol oxalate salt is in a solid crystalline form.

In some embodiments, the mPEG$_7$-O-naloxol oxalate salt crystalline form is in a 1:1 acid to base form.

In certain embodiments, the methods comprises the steps of dissolving mPEG$_7$-O-naloxol free base in a first solvent comprising ethanol and methyl t-butyl ether (MTBE), adding oxalic acid in methyl t-butyl ether to the dissolved mPEG$_7$-O-naloxol, optionally seeding the mixture, to produce a slurry, and filtering the slurry to yield the naloxol-polyethylene glycol conjugate oxalate salt in solid form. Typically, the resulting solid is washed and dried, which can be performed according to standard procedures known to those skilled in the art.

In certain embodiments, dissolving mPEG$_7$-O-naloxol free base in a solvent comprises dissolving mPEG$_7$-O-naloxol free base in 1-5 relative volumes of ethanol, preferably 2 relative volumes of ethanol, and adding 5-15 relative volumes of MTBE, preferably 8 relative volumes of MTBE, to the dissolved mPEG$_7$-O-naloxol in ethanol solution.

In some embodiments, the oxalic acid, dissolved in 5-15 relative volumes of MTBE, preferably 10 relative volumes, is added to the dissolved mPEG$_7$-O-naloxol solution over a period of at least 2 hours to produce a slurry. In some embodiments, the oxalic acid is added over a period of at least 5 hours. In some embodiments, the oxalic acid is added at a temperature of between about 0° C. to about 50° C., between about 15° C. to about 30° C., between about 15° C. to about 25° C. or, in some embodiments, at a temperature of about 20° C.

In certain embodiments, the methods comprises the steps of dissolving mPEG$_7$-O-naloxol free base in a first solvent comprising acetonitrile and water, adding oxalic acid in ethyl acetate to the dissolved mPEG$_7$-O-naloxol, optionally seeding the mixture, to produce a slurry, and filtering the slurry to yield the naloxol-polyethylene glycol conjugate oxalate salt in solid form. Typically, the resulting solid is washed and dried, which can be performed according to standard procedures known to those skilled in the art.

In certain embodiments, dissolving mPEG$_7$-O-naloxol free base in a solvent comprises dissolving mPEG$_7$-O-naloxol free base in 1-5 relative volumes of acetonitrile preferably 2 relative volumes of acetonitrile and adding 0.5-8 equivalents of water, preferably 3 equivalents of water, to the dissolved mPEG$_7$-O-naloxol in the solution.

In some embodiments, dissolving mPEG$_7$-O-naloxol free base in 2 relative volumes of acetonitrile and adding 3 equivalents of water to the dissolved mPEG$_7$-O-naloxol solution; and adding oxalic acid in ethyl acetate to the dissolved mPEG$_7$-O-naloxol over a period of at least 2 hours to produce a slurry; and filtering the slurry to yield the naloxol-polyethylene glycol conjugate oxalate salt in solid form.

In some embodiments, the oxalic acid, dissolved in 5-15 relative volumes of ethyl acetate, preferably 11 relative volumes, is added to the dissolved mPEG$_7$-O-naloxol solution over a period of at least 2 hours to produce a slurry. In some embodiments, the oxalic acid is added over a period of at least 5 hours. In some embodiments, the oxalic acid is added at a temperature of between about 0° C. to about 50° C., between about 15° C. to about 30° C., between about 15° C. to about 25° C. or, in some embodiments, at a temperature of about 20° C.

In certain embodiments the slurry is produced with seeding. In other embodiments, the slurry is produced without seeding.

In certain embodiments the slurry is produced with seeding. In other embodiments, the slurry is produced without seeding.

In some embodiments, the mPEG$_7$-O-naloxol salt provided is a phosphate salt. In some embodiments, the mPEG$_7$-O-naloxol phosphate salt is in a crystalline form having an X-ray powder diffraction (XRPD) pattern substantially as that provided in FIG. 1.

In some embodiments, a crystalline mPEG$_7$-O-naloxol phosphate salt is provided having XRPD d values (Å) comprising 21.0 (s); 12.1 (s); 7.9 (s); 6.5 (s); 5.3 (s); 4.83 (s); 4.24 (s); 3.81 (s); and 3.75 (s).

In certain embodiments, the crystalline mPEG$_7$-O-naloxol phosphate salt XRPD d values (Å) comprise 21.0 (s); 12.1 (s); 10.5 (m); 8.2 (m); 7.9 (s); 7.6 (m); 6.5 (s); 6.1 (m); 5.9 (m); 5.3 (s); 5.2 (m); 5.0 (m); 4.83 (s); 4.54 (w); 4.24 (s); 3.81 (s); 3.75 (s); 3.35 (m); and 3.12 (m). In yet other embodiments, the mPEG$_7$-O-naloxol phosphate salt XRPD d values (Å) are 21.0 (s); 12.1 (s); 10.5 (m); 9.8 (w); 8.2 (m); 7.9 (s); 7.6 (m); 6.5 (s); 6.1 (m); 5.9 (m); 5.3 (s); 5.2 (m); 5.0 (m); 4.83 (s); 4.54 (w); 4.24 (s); 4.09 (w); 4.02 (w); 3.98 (w); 3.81 (s); 3.75 (s); 3.64 (w); 3.58 (w); 3.53 (w); 3.35 (m); and 3.12 (m).

In some embodiments, a crystalline mPEG$_7$-O-naloxol phosphate salt is provided having XRPD 2θ peak (°) values at 4.20 (s); 7.29 (s); 8.42 (m); 10.83 (m); 11.13 (s); 11.63 (m); 13.71 (s); 14.58 (m); 14.96 (m); 16.59 (s); 17.18 (m); 17.62 (m); 18.37 (s); 23.38 (s); 23.75 (s); 26.64 (m); and 28.61 (m). In certain embodiments, the crystalline mPEG$_7$-O-naloxol phosphate salt XRPD 2θ peak (°) values are 4.20 (s); 7.29 (s); 8.42 (m); 9.03 (w); 10.83 (m); 11.13 (s); 11.63 (m); 13.71 (s); 14.58 (m); 14.96 (m); 16.59 (s); 17.18 (m); 17.62 (m); 18.37 (s); 19.55 (w); 20.94 (s); 21.73 (w); 22.14 (w); 22.34 (w); 23.38 (s); 23.75 (s); 24.47 (w); 24.87 (w); 25.20 (w); 26.64 (m); and 28.61 (m).

In another aspect, provided herein are methods of producing a naloxol-polyethylene glycol conjugate phosphate salt, wherein the salt comprises ionic species of mPEG$_7$-O-naloxol and phosphoric acid, which have the formula:

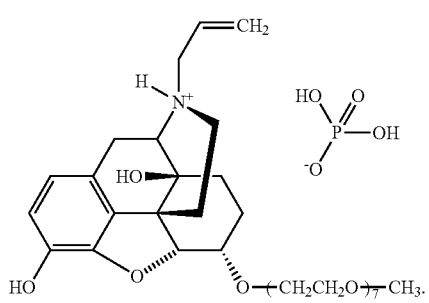

In other embodiments, an mPEG$_7$-O-naloxol phosphate salt is provided. In some embodiments, the mPEG$_7$-O-naloxol phosphate salt is in a solid form, which can, for example, be in an amorphous form, single crystalline form, multi-crystalline form, or mixed amorphous and crystalline form. Preferably, the mPEG$_7$-O-naloxol phosphate salt is in a solid crystalline form.

In some embodiments, the mPEG$_7$-O-naloxol phosphate salt crystalline form is in a 1:1 acid counterion to mPEG$_7$-O-naloxol cation form.

In another aspect, a method of preparing an mPEG$_7$-O-naloxol phosphate salt is provided herein. For instance, an mPEG$_7$-O-naloxol phosphate salt can be prepared by dissolving mPEG$_7$-O-naloxol free base in ethanol and adding MTBE to the dissolved mPEG$_7$-O-naloxol free base. Phosphoric acid in MTBE is added to the dissolved mPEG$_7$-O-naloxol free base. Optionally, the dissolved mPEG$_7$-O-naloxol solution may be seeded. Typically, the phosphoric acid is added slowly over a period of about 2 hours, more typically over 5 or more hours. Once the phosphoric acid is added, the mixture is allowed to stand at 10° C. for over 2 hours, producing a slurry. The slurry is filtered to yield the mPEG$_7$-O-naloxol conjugate phosphate salt in solid form. Typically, the resulting solid is washed and dried, which can be performed according to standard procedures known to those skilled in the art.

In certain embodiments, the mPEG$_7$-O-naloxol free base is dissolved in 2 relative volumes of ethanol and 8 relative volumes of MTBE prior to addition of the phosphoric acid. In certain embodiments, 1.01 equivalents of phosphoric acid are added to the dissolved mPEG$_7$-O-naloxol free base.

In some embodiments, an mPEG$_7$-O-naloxol salt crystalline form provided herein (for example, a phosphate or an oxalate salt) is in a hydrate form. In other embodiments, the mPEG$_7$-O-naloxol salt crystalline form is in a non-solvated (e.g., non-hydrated) form. In some embodiments, the mPEG$_7$-O-naloxol salt crystalline form is a solvate or a hydrate.

In certain embodiments, a naloxol-polyethylene glycol conjugate (e.g., mPEG$_7$-O-naloxol) oxalate salt prepared according to the methods described herein is provided.

In some embodiments, solid salt forms of mPEG$_7$-O-naloxol, including its phosphate or oxalate salt forms, provided herein can be prepared using techniques other than those provided herein, such as those techniques as known in the art, including, but not limited to, melt cooling, rapid melt cooling, freeze drying, spray drying, roller drying, lyophilization, quench cooling the melt, rapid solvent evaporation, slow solvent evaporation, solvent crystallization, slurry recrystallization, melt crystallization, desolvation, sublimation, recrystallization in confined spaces (e.g., in nanopores or capillaries), recrystallization on surfaces or templates (e.g., on polymers), recrystallization in the presence of additives (e.g., co-crystal counter-molecules), dehydration, rapid cooling, slow cooling, vapor diffusion, grinding, cryo-grinding, solvent-drop grinding, microwave-induced precipitation, ultrasonication-induced precipitation, laser-induced precipitation, reaction crystallizataion, antisolvent addition and precipitation from a supercritical fluid.

In some embodiments of a solid mPEG$_7$-O-naloxol salt provided herein (e.g., a phosphate or an oxalate salt), the salt is in a substantially pure crystalline form. For instance, in various subembodiments, a crystalline mPEG$_7$-O-naloxol salt can have a purity of at least about 84%, at least about 85%, at least about 90%, at least about 95%, at least about 97%, at least about 98%, at least about 99%, at least about 99.2%, at least about 99.5%, at least about 99.6%, at least about 99.7% or at least about 99.8% by weight of a single crystalline form, the remainder of the total weight which may be other crystalline or amorphous forms and/or other compounds (such as, for example, an oxidative degradation product).

In certain embodiments, the crystalline mPEG$_7$-O-naloxol salt is substantially free of glycidaldehyde. In some embodiments, the crystalline mPEG$_7$-O-naloxol salt has less then about 100 ppm, less than about 50 ppm, less than about 25 ppm, less than about 5 ppm, less than about 2 ppm or less than about 1 ppm, of glycidaldehyde, for instance, when the crystalline mPEG$_7$-O-naloxol salt is stored at 40° C. for 4 weeks. In various embodiments, the crystalline mPEG$_7$-O-naloxol salt substantially free of glycidaldehyde provided herein is stable. "Stable" as used herein, means that the crystalline mPEG$_7$-O-naloxol salt comprises less than about 100 ppm, less than about 50 ppm, less than about 25 ppm, less than about 5 ppm, less than about 2 ppm, less than about 1 ppm, or is substantially free of glycidaldehyde when the crystalline mPEG$_7$-O-naloxol salt is stored at 40° C. for 4 or more weeks.

In certain embodiments, an mPEG$_7$-O-naloxol oxalate salt is provided, wherein the salt is in crystalline Form A. mPEG$_7$-O-naloxol oxalate salt of Form A exhibits an XRPD pattern substantially such as that shown in FIG. 2.

In certain embodiments, an mPEG$_7$-O-naloxol oxalate salt is provided, wherein the salt is in crystalline Form B. mPEG$_7$-O-naloxol oxalate salt of Form B exhibits an XRPD pattern such as that shown in FIG. 3.

In some embodiments, a crystalline mPEG$_7$-O-naloxol oxalate salt is provided having XRPD d values (Å) comprising 13.2 (s); 6.6 (s); and 4.39 (s).

In certain embodiments, the crystalline mPEG$_7$-O-naloxol oxalate salt XRPD d values (Å) comprise 13.2 (s); 7.9 (m); 7.0 (m); 6.6 (s); 6.0 (m); 5.7 (m); 5.2 (m); 5.1 (m); 4.44 (m); 4.39 (s); 3.95 (m); 3.88 (m); 3.63 (m); and 3.43 (m). In yet other embodiments, the crystalline mPEG$_7$-O-naloxol oxalate salt XRPD d values (Å) are 13.2 (s); 12.0 (w); 9.7 (w); 9.4 (w); 8.3 (w); 8.2 (w); 7.9 (m); 7.4 (w); 7.0 (m); 6.6 (s); 6.0 (m); 5.7 (m); 5.6 (w); 5.4 (w); 5.2 (m); 5.1 (m); 4.91 (w); 4.86 (w); 4.78 (w); 4.71 (w); 4.48 (w); 4.44 (m); 4.39 (s); 4.17 (w); 4.09 (w); 3.95 (m); 3.91 (w); 3.88 (m); 3.69 (w); 3.63 (m); 3.43 (m); 3.29 (w); 3.14 (w); and 3.01 (w).

In some embodiments, a crystalline mPEG$_7$-O-naloxol oxalate salt is provided having XRPD 2θ peak (°) values at 6.72 (s); 11.24 (m); 12.65 (m); 13.44 (s); 14.72 (m); 15.61 (m); 17.01 (m); 17.34 (m); 19.98 (m); 20.21 (s); 22.50 (m); 22.93 (m); 24.53 (m); and 25.99 (m). In certain embodiments, the crystalline mPEG$_7$-O-naloxol oxalate salt XRPD 2θ peak (°) values are 0.6.72 (s); 7.35 (w); 9.13 (w); 9.37 (w); 10.72 (w); 10.82 (w); 11.24 (m); 12.02 (w); 12.65 (m); 13.44 (s); 14.72 (m); 15.61 (m); 15.95 (w); 16.53 (w); 17.01 (m); 17.22 (w); 17.34 (m); 18.06 (w); 18.25 (w); 18.56 (w); 18.86 (w); 19.81 (w); 19.98 (m); 20.21 (s); 21.33 (w); 21.75 (w); 22.50 (m); 22.72 (m); 22.93 (m); 24.14 (w); 24.53 (m); 25.99 (m); 27.07 (w); 28.40 (w); and 29.64 (w).

In certain embodiments, a crystalline mPEG$_7$-O-naloxol oxalate salt is provided exhibiting a single endothermic peak on a differential scanning calorimeter between room temperature and about 150° C., wherein the single endothermic peak maximum occurs between about 84° C. to about 96° C. In certain embodiments, the endothermic peak is between about 89° C. to about 95° C., between about 92° C. to about 93° C. or at about 89° C., about 90° C., about 91° C., about 92° C., about 92.5° C., or at about 93° C., and its ΔH is between about 84 J/gram to about 97 J/gram, or at about 96.1 J/gram.

It will be recognized that, in their solid forms, mPEG$_7$-O-naloxol salts provided herein (e.g., oxalate salts) can exhibit desirable characteristics for the preparation, processing and/or storage of a pharmaceutical composition or drug product. As such, in another aspect, pharmaceutical compositions are provided that comprise an mPEG$_7$-O-naloxol salt. In some embodiments, a pharmaceutical composition is provided comprising an mPEG$_7$-O-naloxol salt and a pharmaceutically acceptable excipient and/or carrier. The choice of excipient, to a large extent, depends on factors, such as the particular mode of administration, the effect of the excipient on the solubility and stability of the active ingredient, and the nature of the dosage form.

Exemplary solids include granules, pellets, beads, powders, which can be administered "as is" or formulated into one or more of the following for administration to a patient: a tablet; a capsule; a caplet; a suppository; and a troche. Preferably, the composition will be in a unit dosage form to thereby provide a unit dosage suitable for single administration of a dosage of mPEG$_7$-O-naloxol in the unit dosage form. Suitable pharmaceutical compositions and dosage forms may be prepared using conventional methods known to those in the field of pharmaceutical formulation and described in the pertinent texts and literature, e.g., *Remington: The Science and Practice of Pharmacy*, 21$^{st}$ edition (Lippincott Williams & Wilkins, Philadelphia, Pa., 2005).

Oral dosage forms are preferred and include, for instance, tablets and capsules. Tablets can be manufactured using standard tablet processing procedures and equipment. Preferred techniques for forming tablets include direct compression and granulation. In addition to mPEG$_7$-O-naloxol salt, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

In some instances, the tablet can be in the form of a uniform tablet. In uniform tablets, the formulation used in preparing the tablet is a substantially homogenous mixture of one or more active agents and one or more pharmaceutical excipients (e.g., diluent). The formulation is then used to make tablets using a suitable tableting process to thereby result in a tablet that is substantially homogenous throughout the tablet.

In still other instances, the tablet can also take the form of a layered tablet (of one, two, three or more layers). The method for manufacturing the layered tablet can include combining two different formulations (e.g., one formulation containing an opioid agonist and another containing the mPEG$_7$-O-naloxol salt) and compressing the two together to form the tablet. Multiple layered tablets of three or more layers are also possible and can be formed, for example, in a similar manner by combining three or more distinct formulations and followed by compression. Capsules are also suitable oral dosage forms, in which case the mPEG$_7$-O-naloxol salt may be encapsulated in a semi-solid or solid form (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, supra, which describes materials and methods for preparing encapsulated pharmaceuticals.

Exemplary excipients include, without limitation, those selected from the group consisting of carbohydrates, inorganic salts, antimicrobial agents, anti-oxidants, surfactants, buffers, acids, bases, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as TWEEN 20 and TWEEN 80, and PLURONICS such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

In addition to mPEG$_7$-O-naloxol salt, the pharmaceutical composition may comprise an opioid agonist. The amount of the active agents (i.e., opioid agonist and mPEG$_7$-O-naloxol salt) in the composition will vary depending on a number of factors, but will optimally be a therapeutically effective dose of each active agent when the composition is stored in a unit dose form. A therapeutically effective dose for each active agent can be determined experimentally by repeated administration of increasing amounts of the active agent in order to determine which amount produces a clinically desired endpoint.

In other embodiments, the unit dose form will comprise both the mPEG$_7$-O-naloxol salt and the opioid agonist, wherein the mPEG$_7$-O-naloxol salt is present in an amount such that significant inhibition of the central analgesic effect of said opioid does not occur when the composition is administered to a subject.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Exemplary excipients are described, for instance, in *Handbook of Pharmaceutical Excipients*, $5^{th}$ Edition (Rowe et al., editors; American Pharmaceutical Association Publications, Washington D.C., 2005). In another aspect, provided herein is a method for administering a composition as provided herein to a patient suffering from a condition that is responsive to treatment with an opioid agonist. Preferably, this method comprises administering a unit dosage form as described herein. The method of administering may be used to treat any condition that can be remedied or prevented by administration of the opioid agonist (e.g., moderate to severe pain). Those of ordinary skill in the art appreciate which conditions an opioid agonist can effectively treat. The actual dose to be administered will vary depend upon the age, weight, and general condition of the subject as well as the severity of the condition being treated, the judgment of the health care professional, and the active agent being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

It is to be understood that while the invention has been described in conjunction with the preferred specific embodiments thereof, that the foregoing description as well as the experimental that follow are intended to illustrate and not limit the scope of the invention.

6. EXAMPLES

Methods and Procedures

Reagents and solvents used below can be obtained from commercial sources such as Aldrich Chemical Co. (Milwaukee, Wis., USA). Solutions of oxalic acid were prepared from oxalic acid dihydrate. Routine chemical and physicochemical analyses were conducted following standard operating procedures known to those skilled in the art. For example, certain analyses were performed as described in the following paragraphs.

XRPD.

In microplate experiments described below, XRPD patterns were collected with BRUKER D-8 DISCOVER diffractometer with BRUKER'S GENERAL AREA DIFFRACTION DETECTION SYSTEM (GADDS, v. 4.1.20). An incident beam of CuK radiation was produced using a fine-focus tube (40 kV, 40 mA), a Goebel mirror and a 0.5 mm double-pinhole collimeter. Diffraction patterns were collected using a HI-STAR area dectector located 15 cm from the sample and processed using GADDS. The intensity in the GADDS image of the diffraction pattern was integrated using a step size of 0.04° 2θ. Prior to analysis a silicon standard was analyzed to verify the Si 111 peak positions.

In other instances XRPD analysis were performed on an INEL SRG-3000 diffractometer, equipped with a curved position-sensitive detector with a 2θ range of 120°. Real time data was collected using CuK α radiation at a resolution of 0.03° 2θ. The tube voltage and amperage were set to 40 kV and 30 mA, respectively. Instrument calibration was performed daily using a silicon reference standard.

In yet other instances, XRPD patterns were collected on an PANALYTICAL X'PERT PRO MPD THETA-THETA system (PANalytical B.V., Almelo, Netherlands) using long-fine-focus Cu Kα-radiation, wavelength of X-rays 1.5418 Å, at 45 kV and 40 mA. A programmable divergence slit and a programmable anti-scatter slit giving an irradiated length of 10 mm were used. 0.02 radian Soller slits were used on the incident and on the diffracted beam path. A 20 mm fixed mask was used on the incident beam path and a nickel-filter was placed in front of a PIXCEL detector using 255 active channels. Thin flat samples were prepared on flat zero background plates made of silicon using a spatula. The plates were mounted in sample holders and rotated in a horizontal position during measurement. Diffraction patterns were collected between 2° 2θ and 50° 2θ in a continuous scan mode. Total time for a scan between 2 and 50° 2θ was approximately 26 minutes. Six scans were collected and a merged scan was calculated by adding the separate scans.

DSC.

Differential scanning calorimetric analyses were carried out on a TA INSTRUMENTS differential scanning calorimeter Q1000. The instrument was calibrated using indium as the reference material. The sample was place into a standard aluminum DSC pan with a non-crimped lid configuration, and the weight recorded. The sample cell was equilibrated at 25° C. and heated under a nitrogen purge at a rate of 10° C./min.

TGA.

Thermogravimetric analyses were performed on a TA INSTRUMENTS 2950 thermogravimetric analyzer. The calibration standards were nickel and ALUMEL. Each sample was placed in an aluminum pan and inserted into the furnace. Samples were started at 25° C. and heated under a stream of nitrogen at a heating rate of 10° C./min.

6.1 Small Scale Experiments

Results of the following small scale experiments exemplify the difficulties in preparing mPEG$_7$-O-naloxol in a solid form. In the small scale experiments explained below, mixtures of mPEG$_7$-O-naloxol and solvent were prepared and assessed for solid formation under various conditions. Potential counterions of a number of acids were tested to assess whether they might form a solid salt with mPEG$_7$-O-naloxol. Over 400 different of acid/solvent combinations were tested in small scale experiments. Table 1 summarizes the acid counterions tested in the small scale experiments. In Table 1, acid counterions indicated with superscript were also tested in scaled up salt experiments. As explained in Section 6.2 below, when scaling up from the small scale experiments to larger scale experiments, it was only possible to isolate solid forms of the phosphate and oxalate salts.

TABLE 1

Acids Used in Small Scale Salt Experiments

| | | | |
|---|---|---|---|
| Acetic | Gentisic | Malonic[1] | Pamoic[1] |
| Adipic[1] | Glutaric | Methanesulfonic[1] | Phosphoric[1,] |
| Benzenesulfonic | Glycolic | 1,5-Naphthalenedisulfonic | Pyroglutamic |
| Benzoic | Hexanoic | 2-Naphthalenesulfonic | Succinic |
| Camphoric | Hippuric | 1-Hydroxy-2-Napthoic | Stearic |
| Citric | Hydrobromic | 3-Hydroxy-2-Napthoic | Sulfuric |
| Decanoic[1] | Hydrochloric | Nicotinic | D-Tartaric[1] |
| Ethanesulfonic[1] | α-Ketoglutaric | Octanoic | L-Tartaric |
| 1,2-Ethanedisulfonic | Maleic[1] | Orotic | Toluenesulfonic[1] |
| Formic | D-Malic | Oxalic[1] | Trifluoroacetic |
| Fumaric[1] | L-Malic[1] | Palmic | |

[1]Also tested in scaled up salt experiments.

Manual Experiment #1.

Using MICROSCREEN™ technology (SSCI, a division of Aptuit, West Lafayette, Ind., USA), mixtures were made by adding an acid counterion to a small amount of mPEG$_7$-O-naloxol in one of five solvents (acetone, DCM, EtOAc, MeOH or THF) to wells of a microplate. The mixtures had a 1:1 molar ratio of mPEG$_7$-O-naloxol to acid. Thirteen acid counterions were assessed in at least one of the solvents (e.g., pyroglutamic acid was tested in MeOH; benzoic acid was tested in each of the five solvents), where most of the counterions were tested in at least three different solvents. Clear solutions were observed in each well after adding the counterion indicating that no immediate solid precipitation was produced. One of two wells containing the same solvent/counterion combination was subjected to fast evaporation conditions and the other well to slow evaporation conditions. In each well, after allowing evaporation, only oils were observed. A different set of acid counterions were tested in manual experiment #2, described below.

Manual Experiment #2.

A set of 13 acid counterions was assessed in a manual microplate method using SSCI's MICROSCREEN™ technology in which wells contained mPEG$_7$-O-naloxol in one of the following five solvents: acetone, EtOAc, MeOH, THF and diethyl ether. Certain wells of the microplate containing mPEG$_7$-O-naloxol and solvent did not have any acid counterion added. In wells to which acid was added, each acid was tested in combination with acetone, MeOH and THF. Some acids were also added to wells containing EtOAc or ether. Except for one well, clear solutions were observed in the wells. The exception was a cloudy mixture produced when maleic acid was added to well containing ether and mPEG$_7$-O-naloxol. After the contents of the wells were allowed to evaporate, however, only oils were observed. Thereafter, solvent was added to each well and the mixtures sonicated. The mixtures were sonicated in two second bursts and allowed to rest for 50 seconds. A total of 20 sonication cycles were completed. Sonication did not result in formation of solids. The mixtures were allowed to evaporate under fast evaporation conditions, and again, only oils were observed. Next, the contents of the microplate were exposed to 45° C., under vacuum, for approximately 20 hours. Oil was observed in each well, however, in about 70 out of the 95 wells there also appeared to be small particles suspended in oil. The entire plate was analyzed by XRPD. No crystalline reflections were observed.

Automated Experiments.

mPEG$_7$-O-naloxol was dissolved in methanol to provide a 0.1 M solution. Selected acids were dissolved in methanol to provide 0.1 M solutions. Using four 96-well microplates prepared within an within an automated platform (Symyx Technologies, Inc., Santa Clara, Calif., USA) specified amounts of mPEG$_7$-O-naloxol and stoichiometric amounts of acid counterion were distributed into about 70 wells in each of the sealed microplates. The same set of 34 acids was added to wells on each of the four microplates. Methanol was then removed from the microplates using a centrifugal vacuum evaporator at room temperature for approximately 30 minutes. Microplates were examined under a light microscope for the presence of solids. Selected solvents or solvent mixtures were then autodispensed into appropriate wells of the microplates.

On microplates 1-3, each acid was tested with in combination with at least one solvent, most against 3 or 4 solvents selected from THF, 2-propanol, 1,4-dioxane, propionitrile, ethanol, 1-butanol and methanol. Microplates 1-3 were sealed and heated in an oven at 40° C. for approximately 30 minutes. The microplates were then agitated at ambient conditions on an orbital shaker for approximately 1 hour. Contents of microplate 1 were subject to fast evaporation by placing the microplate in a fume hood, and solvent allowed to evaporate under ambient conditions. Contents of microplate 2 were subject to slow evaporation by applying an adhesive backed aluminum foil cover (one pin hole per well) to the top of the microplate, placing the microplate in a fume hood, and allowing the solvent to evaporate under ambient conditions. Contents of microplate 3 were subject to sonication, then the solvent allowed to evaporate under slow evaporation conditions explained for microplate 2.

On microplate 4, the acids were tested in combination with 30 µl of solvent which was isopropyl ether in one well and, in another well, acetonitrile. Contents on microplate 4 were subject sonication and then subject to slow evaporation, as previously described.

Wells of microplates 1-4 were examined under light microscope for presence of solids. A large majority of wells on microplates 1-4 did not appear to contain any viable candidate solid salt forms. This observation was also made for wells containing mPEG$_7$-O-naloxol free base and solvent to which no acid counterion was added. However, in a few of the wells where phosphoric, oxalic or pamoic acids were added, solids appeared to be present.

Experiments with 1-Propanol, Ethyl Acetate or THF/Water (9:1).

In small vials, the oil of mPEG$_7$-O-naloxol free base (100 mg) was dissolved in 1 ml of 1-propanol, ethyl acetate or THF/water (9:1). The counter ions were added to the vials, which were stirred by magnetic bars at room temperature for at least one week. The vials were observed from time to time and if a precipitate appeared the vial was sampled and analyzed by XRPD. Slurry tests were run in three series as provided in Tables 2-4. In these tables, "no reaction observed" means any of unsolved starting material, amorphous material or clear solution; "clear solution" means that no solids were observed and "gel (amorphous)" means that while solids were observed in the slurry produced, the solids were amorphous as determined by XRPD.

TABLE 2

Results Using Acid:Base Ratio of 1:1

| Acid | 1-Propanol | Ethyl Acetate | THF/Water (9:1) |
|---|---|---|---|
| L-Tartaric acid | No reaction observed | No reaction observed | clear solution |
| D-Tartaric acid | Gel (amorphous) | No reaction observed | clear solution |
| Fumaric acid | No reaction observed | Counter ion | clear solution |
| Maleic acid | No reaction observed | Gel (amorphous) | clear solution |
| Succinic acid | No reaction observed | Counter ion | clear solution |
| DL-Malic acid | No reaction observed | Counter ion | clear solution |
| Orotic acid | Counter ion | Counter ion | Counter ion |
| Pamoic acid | No reaction observed | Sticky matter | clear solution |
| Malonic acid | No reaction observed | No reaction observed | clear solution |
| L-Malic acid | No reaction observed | No reaction observed | clear solution |
| D-Malic acid | No reaction observed | No reaction observed | clear solution |
| Adipic acid | No reaction observed | Sticky matter | clear solution |
| Citric acid | No reaction observed | No reaction observed | clear solution |

Counter ion - The solid form is the counter ion itself.

TABLE 3

Results Using Acid:Base Ratio of 2:1

| Acid | Ethyl Acetate |
|---|---|
| L-Tartaric acid | Sticky matter |
| D-Tartaric acid | Sticky matter |
| Fumaric acid | Sticky matter |
| Maleic acid | Clear solution + single particles |
| DL-Malic acid | Precipitate |
| Orotic acid | Sticky matter |
| Pamoic acid | Counter ion |
| Malonic acid | clear solution |
| D-Malic acid | Sticky matter |
| Adipic acid | Precipitate |
| Citric acid | Sticky matter |

TABLE 4

| Acid | Acid:Base | Ethyl Acetate |
|---|---|---|
| Phosphoric acid | 1:1 | Gel (amorphous) |
| Phosphoric acid | 2:1 | Gel (amorphous) (1:1 salt) |
| Sulfuric acid | 1:1 | Sticky matter |
| Sulfuric acid | 2:1 | Sticky matter |
| Acetic acid | 1:1 | Clear solution |
| Formic acid (>90%) | 1:1 | Clear solution |
| Methansulfonic acid | 1:1 | Clear solution |
| Benzenesulfonic acid | 1:1 | Clear solution + single particles |
| Hydrobromic acid (48%) aq | 1:1 | Amorphous precipitate |
| Hydrochloric acid, aq | 1:1 | Clear solution |
| 1,2-Ethanedisulfonic acid | 1:1 | Gel amorph (less viscous than phosphate) |
| 1,2-Ethanedisulfonic acid | 2:1 | Gel amorph (less viscous than phosphate) |
| Stearic acid | 1:1 | Counter ion |

As indicated in Tables 2-4, in most of the vials either the acid itself crystallized or there was no crystallization. In some vials a gel was formed. In two of these cases, with D-tartaric acid and 1,2-ethanedisulfonic acid, crystalline material may have been formed based on observation by microscopy but became a liquid when isolated from scaled up tests.

After one week the vials with no precipitate were left to slowly evaporate. No crystalline phase was observed, other than that observed with phosphoric acid.

Experiments with mPEG$_7$-O-Naloxol Free Base.

mPEG$_7$-O-naloxol was dissolved in each of the solvents, ethyl acetate, 1-propanol and THF/water (9:1) in concentrations of 100 mg/ml and 500 mg/ml. No crystallization was observed for 3 weeks at 20° C. The samples were then treated with sonification, evaporation, antisolvent addition and put into freezer, without result. The free base was also tested in heptane, toluene and hexane by allowing the solvents to evaporate, with the result that no crystallization was observed.

Results of small scale experiments indicated that, by far, the large majority of combinations of different solvents, potential acid counterions and conditions tested would not produce a solid form of mPEG$_7$-O-naloxol. A few of the acids, at least in certain combinations, suggested that a solid salt form might be possible. These acids were tested in scaled up experiments to assess their potential for forming a solid mPEG$_7$-O-naloxol salt form.

6.2 Scaled Up Experiments

Several acids, including adipic, decanoic, fumaric, maleic, malonic, methanesulfonic, oxalic, pamoic, phosphoric and toluenesulfoic, were chosen for scale-up attempts for producing mPEG$_7$-O-naloxol salts at approximately 30 mg each. Solvents used in these experiments included THF, n-hexanes, cyclohexane, EtOAc, ether, DCM, IPE, acetonitrile, MeOH, PrCN, butanol, acetone, and mixtures thereof. In most instances, the mixture of mPEG$_7$-O-naloxol and acid in solvent produced a clear solution. Some exceptions, were, for example, where mixtures included L-malic acid or malonic acid and EtOAc, toluene-sulfonic acid and hexanes, and oxalic in some solvents. The mixtures were subject to various conditions intended to assist in producing a precipitate, which are briefly described in the following paragraphs.

Crash Cool—

Saturated solutions were filtered through a 0.2 μm nylon filter into a vial. Vials were then either left at ambient temperature or placed in the refrigerator.

Fast Evaporation—

Solutions were sonicated between aliquot additions to assist in dissolution. Once a mixture reached dissolution, as judged by visual inspection, the solution was filtered through a 0.2 μm nylon filter. The filtered solution was allowed to evaporate at ambient temperature in an uncapped vial.

Slow Cool—

Saturated solutions were filtered through a 0.2 μm nylon filter into a vial. In vials where there were no solids present, or if the amount of solids was judged too little for XRPD analysis, the vial was placed in a refrigerator. Following refrigeration, in those vials where no solids were observed, the vial was placed in a freezer. Any solids that formed during the procedures were isolated by filtration and allowed to dry prior to analysis.

Although results of small scale experiments hinted that maleic, pamoic, D-tartaric and 1,2-ethanedisulfonic acids might form solid salt forms, in the scaled up experiments only an oil was produced with these potential acid counterions, or, when any precipitate was present, the precipitate dissolved or melted when isolated. It was not possible to measure XRPD or confirm salt formation for these potential acid counterions.

The results of the scaled up salt experiments were that, of the potential acid counterions tested, only the phosphoric and oxalic acids were found to produce a solid form that could be characterized. Efforts were directed to determining exemplary preparations of solid phosphate and oxalate salt forms, which are provided below, together with a characterization of each of the solid forms produced.

6.3 Preparation and Characterization of mPEG$_7$-O-Naloxol Solid Forms

The following examples provide exemplary preparations and a characterization of phosphate salt and oxalate salt forms of mPEG$_7$-O-naloxol.

6.3.1 Solid mPEG$_7$-O-Naloxol Phosphate Salt Form

A single solid mPEG$_7$-O-naloxol phosphate salt form was obtained using the following procedures.

Toluene/Heptane Method.

Salt was formed in a mixture of toluene and heptane by addition of 85% w/w (aq.) phosphoric acid in equivalent amount to the free base at about 20° C. In this method, the crystals were small and the filtration time was long. The procedure of solvent addition and the composition of toluene to heptane was difficult to balance. In some experiments oil was formed.

Ethanol/MTBE Method.

In a number of separate preparations, mPEG$_7$-O-naloxol was dissolved in ethanol and MTBE and then phosphoric acid dissolved in MTBE was added to it. The solutions were allowed to evaporate, which in some of the preparations, produced some crystalline phosphate salt. In other preparations an oil formed, which may be due to adding the phosphoric acid solution too fast.

Using crystals from these preparations as seeds, the following steps were taken to prepare crystalline mPEG$_7$-O-naloxol phosphate salt: (1) free base (1 gram) was dissolved in 2 relative volumes of ethanol (2 ml) at 20° C.; (2) 8 rel. vol. (8 ml) MTBE was added to the solution; (3) a phosphoric acid solution was prepared by dissolving 1.01 eq. of the phosphoric acid (99% w/w) in 10 rel. vol. MTBE (10 ml); (4) 3% of the phosphoric acid solution (0.3 rel. vol) was added to the free base solution over 10 minutes at 20° C.; (5) seeds (1% w/w) were added and the solution allowed to stand for at least 30 minutes; (6) the remaining acid solution was added over 5 hours; (7) the solution was cooled to 10° C. over 2 hours, and kept at that temperature for at least 12 hours; (8) the slurry was then filtered; (9) the solid material was washed with MTBE, 10 rel. vol. and dried under vacuum at 20° C. The yield was about 90%. This method was scaled up to 10 L using about 400 grams of mPEG$_7$-O-naloxol resulting in a yield of 94%.

Characterization of Solid State of mPEG$_7$-O-Naloxol Phosphate.

It is an 1:1 salt and only one crystal modification has been observed. The crystallinity of the salt is good as shown by the XRPD (FIG. 1). XRPD pattern data are provided in Table 5.

TABLE 5

XRPD values mPEG$_7$-O-Naloxol Phosphate Salt

| 2θ Angle, ° | d value, Å | Relative Intensity, % | |
|---|---|---|---|
| 4.20 | 21.0 | 40 | s |
| 7.29 | 12.1 | 25 | s |
| 8.42 | 10.5 | 10 | m |

TABLE 5-continued

XRPD values mPEG$_7$-O-Naloxol Phosphate Salt

| 2θ Angle, ° | d value, Å | Relative Intensity, % | |
|---|---|---|---|
| 9.03 | 9.8 | 5 | w |
| 10.83 | 8.2 | 15 | m |
| 11.13 | 7.9 | 40 | s |
| 11.63 | 7.6 | 25 | m |
| 13.71 | 6.5 | 65 | s |
| 14.58 | 6.1 | 45 | m |
| 14.96 | 5.9 | 30 | m |
| 16.59 | 5.3 | 100 | s |
| 17.18 | 5.2 | 30 | m |
| 17.62 | 5.0 | 35 | m |
| 18.37 | 4.83 | 70 | s |
| 19.55 | 4.54 | 30 | w |
| 20.94 | 4.24 | 75 | s |
| 21.73 | 4.09 | 35 | w |
| 22.14 | 4.02 | 35 | w |
| 22.34 | 3.98 | 35 | w |
| 23.38 | 3.81 | 70 | s |
| 23.75 | 3.75 | 60 | s |
| 24.47 | 3.64 | 30 | w |
| 24.87 | 3.58 | 30 | w |
| 25.20 | 3.53 | 25 | w |
| 26.64 | 3.35 | 45 | m |
| 28.61 | 3.12 | 45 | m |

As determined by DSC, the melting onset of mPEG$_7$-O-naloxol phosphate salt is 107.3° C. and the heat of fusion is 33.3 J/g, although the peak is broad. The isotherm curve from the DVS shows continuous (exponential) moisture uptake from the start. The desorption curve is close to the adsorption curve (no hysteresis). Scanning electron microscopy revealed that the solid is composed of small aggregated needles.

When analyzed by NMR, it was observed that chemical shifts with the solution $^1$H-NMR spectra are consistent with salt formation. Proton NMR with an internal standard (sodium formate) indicated that the phosphate salt is an unsolvated mono-phosphate (1:1) salt. Summary of NMR assignments for mPEG$_7$-O-naloxol phosphate salt were as follows.

$^1$H NMR, ppm (multiplicity, number of H, coupling constants in Hz if possible): 1.34 (m, 1H), 1.54-1.67 (m, 2H), 1.73 (dd, 1H, 4, 14), 1.77-1.85 (m, 1H), 2.48 (dt, 1H, 5, 14), 2.89 (dt, 1H, 4, 13), 3.08 (dd, 1H, 7, 20), 3.22 (dd, 1H, 5, 13), 3.35 (s, 3H), 3.38 (d, 1H, 20), 3.50-3.90 (m, 31H), 4.01 (m, 1H), 4.91 (d, 1H, 5), 5.60 (d, 1H, 10), 5.61 (d, 1H, 17), 5.87 (m, 1H), 6.73 (d, 1H, 8), 6.82 (d, 1H, 8).

$^{13}$C NMR, ppm: 20.1, 23.0, 27.2, 29.1, 45.3, 45.8. 55.7, 58.0, 62.4, 69.1, 69.4, 69.51-69.54 (multiple of signals), 69.6, 69.8, 70.5, 70.9, 74.1, 87.2, 118.3, 119.6, 122.3, 125.8, 126.2, 129.2, 137.7, 145.3.

6.3.2 Solid mPEG$_7$-O-Naloxol Oxalate Salt Forms

The following examples describe the preparation and characterization of solid state mPEG$_7$-O-naloxol oxalate salt forms.

Form A.

In scaled-up experiments, summarized in Section 6.2 above, it was noted that a combination of oxalic acid and EtOAc produced a white solid that appeared to be hygroscopic that deliquesced upon filtration. The solid was successfully isolated when filtered under dry nitrogen and characterized by XRPD as provided in FIG. 2. This form was termed mPEG$_7$-O-naloxol oxalate salt solid "Form A."

Form B.

In scaled-up experiments, summarized in Section 6.2 above, it was noted that combinations of oxalic acid with IPE or with MTBE produced a white solid. These observations were reproduced when scaling up from the 30 mg amounts previously used (see Section 6.2, above) to amounts indicated in Table 6. XRPD and other analysis, discussed below, confirmed that the solid form of mPEG$_7$-O-naloxol made from the combinations provided in Table 6 were in a form, termed "Form B," which was different than Form A produced with the combination of oxalic acid and EtOAc.

TABLE 6

Production of Solid State mPEG$_7$-O-Naloxol Oxalate Salt Form B

| Solvent | Approximate Scale | Description | XRPD Result |
|---|---|---|---|
| IPE | 150 mg | White solid | Form B |
|  | 1.5 g (92% yield) | White solid | Form B |
| MTBE | 2.2 g (84% yield) | White solid | Form B |

Using small amounts of the mPEG$_7$-O-naloxol oxalate salt Form B from preparations such as those summarized in Table 6 for seeding, Form B was produced following these steps: (1) dissolve the free base (1 gram) in 2 relative volumes of ethanol (2 ml) at 20° C.; (2) add 8 rel. vol. (8 ml) MTBE to the solution; (3) dissolve 1.01 equivalents of the oxalic acid (98%) in 10 rel. vol. MTBE (10 ml); (4) add 10% of the oxalic acid solution to the free base solution over 5-10 minutes at 20° C. (1.0 rel. vol.); (5) Add seeds, 1% w/w and wait for at least 30 minutes; (5) start the addition of the remaining acid solution over 2 hrs.; (6) after additional ageing for at least 2 hrs., filtrate the slurry; (7) wash with MTBE, 10 rel. vol.; and (8) dry at vacuum and at 20° C. Using the same method, scaled up, Form B was produced with a yield of 93%, with formation of about 400 gram oxalate salt.

In another example form B was produced following the steps: (1) dissolve the free base (400 gram) in 2 relative volumes of acetonitrile (800 ml) and 3.0 equivalents (32.3 ml) water at 20° C.; (2) dissolve 1.01 equivalents (55.46 gram) of oxalic acid (98%) in 11 relative volumes (4400 ml) of ethyl acetate; (3) add 60% of the oxalic acid solution to the free base solution over about 30 minutes at 20° C.; (4) Add seeds, 1% w/w and wait for at least 30 minutes; (5) Start the addition of the remaining acid solution over 2 hrs. at 20° C.; (6) Cool to 10° C. over 1 hr. (7) after additional ageing for at least 1 hr. filter the slurry; (8) wash with a mixture of acetonitrile (1 rel. vol. 400 ml) and ethyl acetate (5.5 rel. vol. 2200 ml) at 10° C.; (9) wash with 2.5 rel. vol. (1000 ml) ethyl acetate at 20° C.; (10) dry at vacuum and 40° C.

The crystallinity of the salt was good as demonstrated by XRPD (FIG. 3). XRPD pattern data for Form B are provided in Table 7.

TABLE 7

XRPD Values for mPEG$_7$-O-Naloxol Oxalate Salt Form B

| 2θ Angle, ° | d value, Å | Relative Intensity, % | |
|---|---|---|---|
| 6.72 | 13.2 | 100 | s |
| 7.35 | 12.0 | 5 | w |
| 9.13 | 9.7 | <5 | w |
| 9.37 | 9.4 | <5 | w |
| 10.72 | 8.3 | <5 | w |
| 10.82 | 8.2 | <5 | w |
| 11.24 | 7.9 | 10 | m |
| 12.02 | 7.4 | 5 | w |
| 12.65 | 7.0 | 5 | m |
| 13.44 | 6.6 | 40 | s |
| 14.72 | 6.0 | 10 | m |
| 15.61 | 5.7 | 15 | m |
| 15.95 | 5.6 | 10 | w |
| 16.53 | 5.4 | 5 | w |
| 17.01 | 5.2 | 15 | m |
| 17.22 | 5.1 | 10 | w |
| 17.34 | 5.1 | 20 | m |
| 18.06 | 4.91 | 5 | w |
| 18.25 | 4.86 | 5 | w |
| 18.56 | 4.78 | 5 | w |
| 18.86 | 4.71 | 5 | w |
| 19.81 | 4.48 | 10 | w |
| 19.98 | 4.44 | 25 | m |
| 20.21 | 4.39 | 100 | s |
| 21.33 | 4.17 | 10 | w |
| 21.75 | 4.09 | 10 | w |
| 22.50 | 3.95 | 35 | m |
| 22.72 | 3.91 | 10 | w |
| 22.93 | 3.88 | 40 | m |
| 24.14 | 3.69 | 5 | w |
| 24.53 | 3.63 | 50 | m |
| 25.99 | 3.43 | 30 | m |
| 27.07 | 3.29 | 5 | w |
| 28.40 | 3.14 | 15 | w |
| 29.64 | 3.01 | 5 | w |

Further analysis of Form B by DSC showed a sharp endothermic peak at 92.5° C. (ΔH is 96.1 J/g), which was confirmed as the melt by hot stage microscopy. Moisture uptake by DVS showed a minor uptake below 70% relative humidity (RH). Above 70% RH there is moisture uptake indicating deliquescence. There was hysteresis during desorption.

Thermogravimetric analysis showed negligible weight loss (~0.3%) up to 90° C. Scanning electron microscopy visualization indicated that the isolated material is composed of aggregates of small crystalline thin plates.

When analyzed by NMR, it was observed that chemical shifts within the solution $^1$H-NMR spectra are consistent with salt formation. Proton NMR with an internal standard (sodium formate) indicated that Form B is an unsolvated monooxalate (1:1) salt. Summary of NMR assignments for mPEG$_7$-O-naloxol oxalate salt were as follows.

$^1$H NMR, ppm (multiplicity, number of H, coupling constants in Hz if possible): 1.35 (m, 1H), 1.55-1.67 (m, 2H), 1.74 (dd, 1H, 4, 14), 1.77-1.85 (m, 1H), 2.49 (dt, 1H, 5, 14), 2.90 (dt, 1H, 4, 13), 3.09 (dd, 1H, 7, 20), 3.23 (dd, 1H, 5, 13), 3.36 (s, 3H), 3.39 (d, 1H, 20), 3.51-3.90 (m, 31H), 4.01 (m, 1H), 4.92 (d, 1H, 5), 5.60 (d, 1H, 10), 5.61 (d, 1H, 17), 5.88 (m, 1H), 6.73 (d, 1H, 8), 6.83 (d, 1H, 8).

$^{13}$C NMR, ppm: 20.0, 23.0, 27.2, 29.1, 45.3, 45.8. 55.7, 58.0, 62.4, 69.1, 69.4, 69.5-69.5 (multiple of signals), 69.6, 69.8, 70.5, 70.9, 74.1, 87.2, 118.3, 119.6, 122.3, 125.8, 126.2, 129.2, 137.7, 145.3, 165.8.

6.4 Stability Studies on mPEG$_7$-O-Naloxol Oxalate Salt Form B

Stability of mPEG$_7$-O-naloxol oxalate salt form B under different storage conditions was assessed by storing individual samples at a temperature ranging from about 5° C. to about 70° C., with varying relative humidity ("RH"), for 2 or 4 weeks, using unsealed bottles without added anti-oxidants. After storage, the samples were visually inspected, its solid state form analyzed by XRPD, and then chemically analyzed by tandem gas chromatography/mass spectrometry (starting samples) or liquid chromatography/mass spectrometry (all other samples) for impurities including glycidaldehyde, as summarized in Table 8. In Table 8, concentrations of glycidaldehyde, an oxidative degradation product of mPEG$_7$-O-naloxol free base, are provided in parts per million (ppm).

TABLE 8

Stabilty of mPEG$_7$-O-Naloxol Oxalate Salt Form B As Compared to mPEG$_7$-O-Naloxol Free Base

| Condition, Time Period | Appearance | Organic Impurities (area %) | XRPD | Glycidaldehyde (ppm) |
|---|---|---|---|---|
| Oxalate salt | | | | |
| Salt, 0 weeks | White powder | 1.74 | Form B | <0.2 |
| 25° C., 60% RH, 2 weeks | White powder | 1.63 | Form B | <5 |
| 25° C., 60% RH, 4 weeks | White powder | 1.62 | Form B | <5 |
| 40° C., 75% RH, 2 weeks | Pale yellow liquid | 1.60 | (liquid) | <5 |
| 40° C., 75% RH, 4 weeks | Pale yellow liquid | 1.67 | (liquid) | <5 |
| 5° C., 4 weeks | White powder | 1.63 | Form B | <5 |
| 40° C., 2 weeks | White powder | 1.57 | Form B | <5 |
| 40° C., 4 weeks | White powder | 1.67 | Form B | <5 |
| 70° C., 2 weeks | Pale yellow powder | 1.64 | Form B | <5 |
| 70° C., 4 weeks | Pale yellow powder | 1.95 | Form B | <5 |
| Free Base | | | | |
| Free base, 0 weeks | Yellow to brown liquid | 2.4 | (oil) | 1.6 |
| 40° C., 4 weeks | Dark yellow liquid | 3.74 | (oil) | 440 |

The results in Table 8 show that at high relative humidity (75% RH), the salt liquefies which, consistent with the DVS analysis of form B (see subsection 6.3.2, above), is likely due to moisture uptake. The impurities associated in the salt were not observed to increase. Unlike the free base in which the concentration of glycidaldehyde increased from 1.6 ppm to about 440 ppm when stored at 40° C., glycidaldehyde was below 5 ppm in all salt samples. No change to the solid state form was observed over time for any of the powder samples.

6.5 Exemplary Pharmaceutical Formulations

Prophetic pharmaceutical formulations comprising solid B mPEG$_7$-O-naloxol oxalate salt form B for oral administration are provided below.

Exemplary Capsule Formulation for Oral Administration.

Ingredients of 30 mg mPEG$_7$-O-naloxol oxalate salt Form B, 50 mg Lactose, 50 mg Starch, 2 mg Talc and 10 mg magnesium stearate, in proper quantity, are mixed, and filled in a gelatin capsule according to conventional preparation for capsules known to those skilled in the art to give a capsule.

Modifications and variations in the subject matter set forth in the above illustrative examples are expected to occur to those skilled in the art. Only such limitations as appear in the appended claims should be placed on any claimed invention.

All publications including books, patents, patent applications and published patent applications cited herein are hereby incorporated by reference in their entireties for all purposes.

What is claimed:

1. A crystalline phosphate salt of mPEG7-O-naloxol having XRPD d values of (Å) comprising 21.0; 12.1; 7.9; 6.5; 5.3; 4.83; 4.24; 3.81; and 3.75.

* * * * *